(12) United States Patent
Munari et al.

(10) Patent No.: US 7,818,994 B2
(45) Date of Patent: Oct. 26, 2010

(54) METHOD AND APPARATUS FOR INJECTING SAMPLES IN GAS CHROMATOGRAPHY

(75) Inventors: Fausto Munari, Rodano (IT); Paolo Magni, Rodano (IT); Koni Grob, Fehraltorf (CH)

(73) Assignee: Thermo Electron S.p.A., Rodano (MI) (IT)

( * ) Notice: Subject to any disclaimer, the term of this patent is extended or adjusted under 35 U.S.C. 154(b) by 853 days.

(21) Appl. No.: 11/596,194

(22) PCT Filed: May 11, 2005

(86) PCT No.: PCT/IB2005/001271

§ 371 (c)(1),
(2), (4) Date: Nov. 13, 2006

(87) PCT Pub. No.: WO2005/116627

PCT Pub. Date: Dec. 8, 2005

(65) Prior Publication Data

US 2008/0257013 A1  Oct. 23, 2008

(30) Foreign Application Priority Data

May 13, 2004 (IT) .......................... MI2004A0962

(51) Int. Cl.
*G01N 1/00* (2006.01)
*G01N 30/12* (2006.01)

(52) U.S. Cl. .................................... 73/23.41

(58) Field of Classification Search ................. 73/23.41, 73/23.39, 23.2, 23.22
See application file for complete search history.

(56) References Cited

U.S. PATENT DOCUMENTS

| 3,247,704 | A | 4/1966 | König |
| 3,859,209 | A | 1/1975 | Jahnsen et al. |
| 5,340,475 | A | 8/1994 | Cortes et al. |
| 6,402,947 | B1 | 6/2002 | Alamirano et al. |
| 7,261,812 | B1 * | 8/2007 | Karp et al. ............... 210/198.2 |
| 2002/0187557 | A1 * | 12/2002 | Hobbs et al. ................ 436/161 |
| 2003/0087454 | A1 * | 5/2003 | Schultz et al. .............. 436/161 |

FOREIGN PATENT DOCUMENTS

DE         12 03 501 B       10/1965

(Continued)

OTHER PUBLICATIONS

Teske et al., "Methods for, and applications of, large-volume injection in capillary gas chromatography", Trends in Analytical Chemistry, vol. 21, No. 9-10, pp. 584-593 (2002).

(Continued)

*Primary Examiner*—Daniel S Larkin
(74) *Attorney, Agent, or Firm*—Nixon & Vanderhye P.C.

(57) ABSTRACT

The present invention relates to a method for injecting a sample (i.e. a material to be analyzed that may be dissolved in a solvent) in a vaporization chamber or in a pre-column or a gas chromatograper, this method implying separately injecting a co-solvent, with the co-solvent being injected in advance of the sample and/or in a point in the vaporization chamber other than the sample injection point.

22 Claims, 2 Drawing Sheets

FOREIGN PATENT DOCUMENTS

EP          0 959 351 A2    11/1999

OTHER PUBLICATIONS

Grob, "Development of the transfer techniques for on-line high-performance liquid chromatography-capillary gas chromatography", Journal of Chromatography A., vol. 703, No. 1, pp. 265-276 (1995).

Grob, Efficiency through combining high-performance liquid chromatography and high resolution gas chromatography progress 1995-1999, Journal of Chromatography A., vol. 892, No. 1-2, pp. 407-420 (2000).

Hankemeier, "Use of a presolvent to include volatile organic analytes in the application range of on-line solid-phase extraction-gas chromatography-mass spectrometry", Journal of Chromatography A., vol. 811, No. 1-2, pp. 117-133 (1998).

* cited by examiner

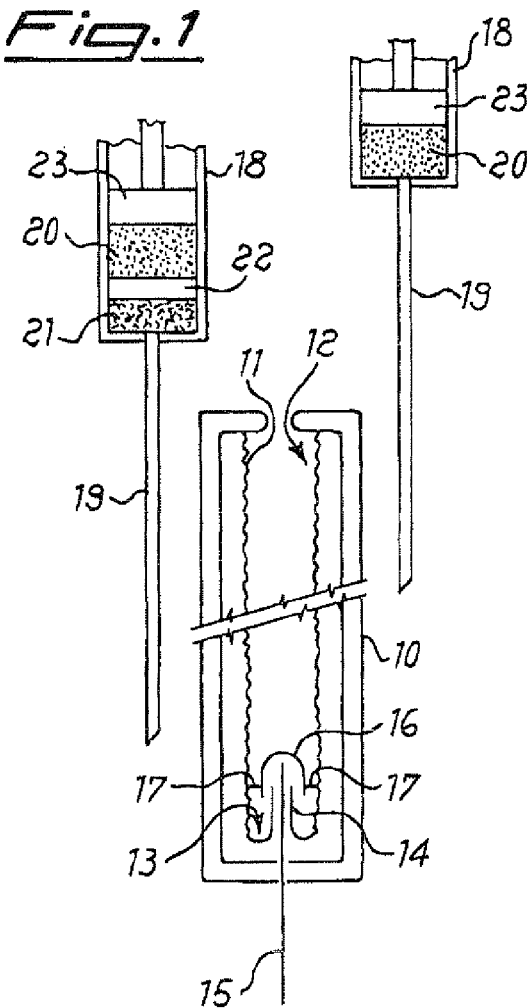
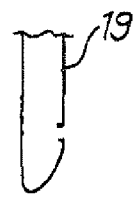
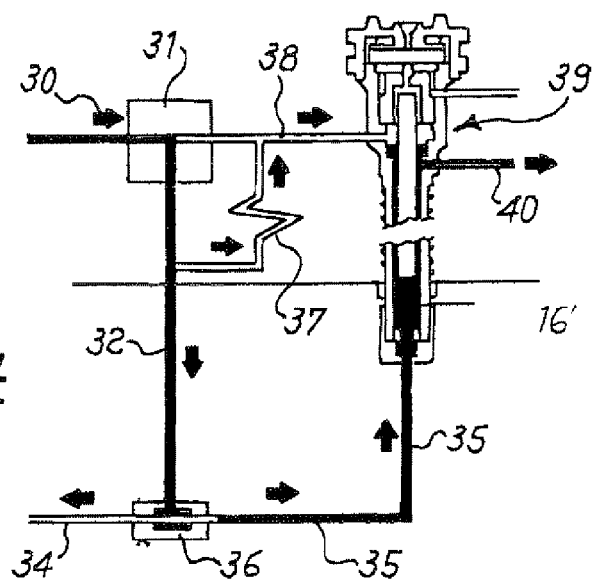

ns in gas chromatography analy-# METHOD AND APPARATUS FOR INJECTING SAMPLES IN GAS CHROMATOGRAPHY This application is the US national phase of international application PCT/IB2005/001271 filed 11 May 2005, which designated the U.S. and claimed priority of IT MI2004A000962 filed 13 May 2004, the entire contents of each of which are hereby incorporated by reference.

BACKGROUND OF THE INVENTION

An apparatus for gas chromatographic analysis essentially consists of an injector, a gas-chromatographic column with stationary phase coating housed in a temperature-controlled oven, and a detector.

A liquid sample consisting of the substances to be analysed and a solvent therefore is introduced in the injector, this sample being directly injected in the gas chromatography column or in a pre-column generally without stationary phase, or in a vaporisation chamber which is independently heated or heatable, where the sample is vaporized before being introduced in the column via a carrier gas.

The current trend is to increase the sample volumes for being able to analyze trace components. However, this implies the formation of important volumes of vaporized solvent, which are normally eliminated before the same enters the gas chromatography column, either at the same injector or at the end of a pre-column.

Eliminating most of the solvent is required, though this entails the risk that the most volatile components of the material to be tested are lost by being entrained by the vaporized solvent.

DESCRIPTION OF THE PRIOR ART

In order to overcome or at least reduce this drawback, it has been suggested to use the so-called solvent effect, or better so called "solvent trapping" in which, essentially, the liquid solvent retains the components (mainly the volatiles) until they are completely vaporized. If the main solvent does not work as required, a co-solvent mixed in the main solvent may be used. See for example: K. Grob and E. Miller "Co-Solvent Effects for Preventing Broadening or Loss of Early Eluted Peaks when Using Concurrent Solvent Evaporation in Capillary GC" Journal of High Resolution Chromatography & Chromatography Communications, vol. II May 1988 pp. 388-394 e K. Grob and D. Fröhlich "Splitless Injection of Large Volumes of Aqueous Samples—A Basic Feasibility Study" Journal of High Resolution Chromatography vol. 16, April 1993 pp. 224-228.

This co-solvent generally has a boiling point higher than the solvent belonging to the sample and is capable of retaining the volatiles of the substance to be analyzed, particularly due to its affinity with them or its position in the injection system.

The co-solvent deposits on the walls of the vaporization chamber or inner liner thereof, or the walls of a pre-column in case of direct injection, thereby forming a film retaining those compounds of the material to be analyzed which have the greatest affinity thereto.

During vaporization and elimination of the main solvent, the co-solvent retains the most volatile substances until they are introduced in the column following the subsequent vaporization of the co-solvent. Obviously, this action improves the analysis of the volatiles, but only in part, because they tend to be eliminated with the main solvent and with the part of co-solvent that inevitably vaporizes and is eliminated with the main solvent.

SUMMARY OF THE INVENTION

In order to improve the effectiveness of the co-solvent, it is now suggested by the present invention that the co-solvent is injected separately from the sample, so that it can be delivered to a position where it is more efficient in retaining the volatile compounds. Thereby, the potentiality of the solvent trapping mechanism is best used, and/or the required amount of co-solvent can be reduced.

Therefore, it is an object of the present invention to provide a method for injecting samples in gas chromatography analyses using co-solvent (either the same as the main solvent, or different), which method allows one to optimize the action of the co-solvent, possibly also reducing the amount thereof, by preventing the same from being mixed with the sample, and to the extent possible, from being eliminated with the main solvent, and by allowing a greater flexibility in defining the rate of the carrier gas and the injection temperature. Within the scope of the present description and claims, by "co-solvent" is meant not only a suitable solvent for the substance to be analyzed, either the same as or (usually) different from that composing the sample, but also a liquid substance selected on the basis of its affinity with the substance to be analyzed, not necessarily being a solvent therefore.

In practice, by injecting the co-solvent prior to the sample, and/or in a different point, the co-solvent can be accumulated in the best condition for performing its function, particularly avoiding that the same is immediately mixed with the main solvent, thereby also avoiding the negative effect of the co-solvent being washed by the main solvent.

The invention applies both in the case where the injections of the co-solvent and the sample are carried out at a lower ambient temperature than the solvent boiling point (corrected based on pressure), and in the case where the injection is carried out at a higher ambient temperature than the solvent boiling point. The first case is represented by the on-column injection and the programmed temperature vaporization injection (PTV). The second case is represented by the conventional vaporizing injectors, either with or without splitting (SSL).

In order to best achieve the objects of the invention, in the above mentioned first case and when the injection of the sample takes place subsequently to the co-solvent, it is suitable that the same is carried out before the pre-injected co-solvent undergoes a substantial evaporation at the temperature in the vaporization chamber or pre-column during the injection. This temperature will be selected based on the nature of the main solvent and co-solvent, such that a great vaporization of the main solvent and a small evaporation of the co-solvent are obtained, particularly when the latter (as is usual) is different from and and has a boiling point higher than the main solvent.

After the main solvent has been eliminated, the temperature in the vaporization chamber or the oven containing the pre-column can be increased in order to accelerate the transfer of the co-solvent and the substances to be analyzed to the gas chromatographic column.

In the cited second case (SSL), by means of the pre-injection of the co-solvent, a cooling is obtained in the area where the sample will be injected, due to the vaporization of the co-solvent, such as to reduce the risk that the thermolabile compounds may deteriorate. A partial vaporization of the co-solvent in the injection needle and then a cooling of this needle has the further advantage of avoiding that the sample may vaporize in the needle, which is undesired in some cases.

With a PTV injector, the injection of the co-solvent is preferably carried out at a higher speed than the injection of the sample, and possibly with a bent spray needle such that the co-solvent can be deposited in the desired area, i.e. the liner walls, thereby it is not injected towards the bottom. Thus, the sample comes in contact with the co-solvent mainly in the vapour phase.

Finally, the co-solvent and the sample can be injected with only one syringe, possibly by interposing therein an air cushion between the former and the latter, or the co-solvent and sample can be injected in different points by means of a special syringe and a double needle, or also by means of a syringe moved between both injections.

Obviously, the co-solvent and sample can be also injected by means of different syringes, the sample can be also injected in subsequent metered amounts to avoid overloading the injector. Furthermore, multiple injections of co-solvent can be carried out, which are intercalated with injections of the sample, such that a suitable amount of co-solvent can be constantly maintained.

The method described above is preferably carried out using an injector associated with a sampler capable of automatically carrying out the injection of the co-solvent and sample in two different points and/or at different times and preferably at different but programmable and controlled speeds. The co-solvent can be also at least partially injected while the needle is moving, i.e. towards the sample injection point.

Still in case of using PTV injectors or on-column direct injection, injecting the co-solvent in advance can be advantageous in order to hold gases or vapours injected in this physical state, as it is the case with thermally-desorbed samples, also in replacement of the cold trap that can be provided in this case to re-condensate the sample.

DESCRIPTION OF PREFERRED EMBODIMENTS

In a case of a PTV vaporizing injector, this will preferably have an inner liner configured as shown in the following figures, which also show a particular configuration of the carrier gas feeding system.

More in detail:

FIG. 1 is a schematic diagram of a vaporizing injector with a preferred inner liner of its chamber which is particularly suitable to carry out the method according to the invention, together with a schematic diagram of the operating modes of the sampler associated therewith.

FIG. 2 is a schematic view of a preferred configuration of the needle tip.

FIG. 4 shows the diagram of a PTV injector (Programmed Temperature Vaporizer) which is particularly suitable to implement the present invention.

BRIEF DESCRIPTION OF THE PREFERRED EMBODIMENTS

Figure 3:
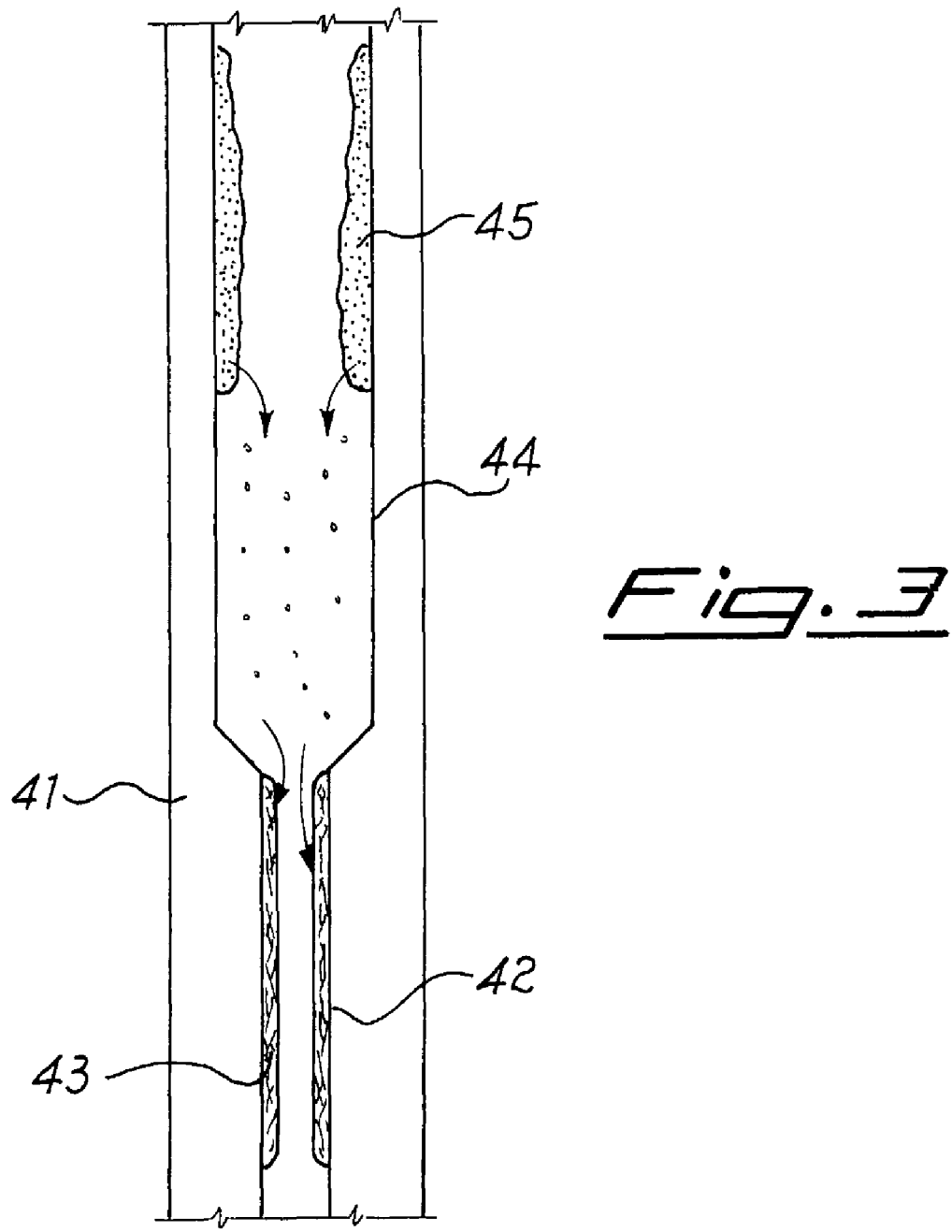
FIG. 3 is a schematic diagram of a vaporizer with an alternative inner liner as compared with FIG. 1.

With reference to the annexed figures, an exemplary application of the present invention in a PTV injector is illustrated.

It should be noted, however, that the invention can be also applied in an on-column injector, where direct introduction is provided in a pre-column that is open towards the injector and connected downstream with a gas chromatographic column. In this case, the injections of co-solvent and sample are carried out according to the procedure described above, i.e. a pre-injection of co-solvent and a subsequent injection of the sample.

Again, the invention can be also applied to an SSL injector, in which, during the injection, the vaporization chamber is at a temperature above the solvent (and generally the co-solvent, too) boiling point, in order to achieve the advantages mentioned above.

In the case of a PTV vaporizing injector, the injection of the co-solvent is carried out in advance and/or in a point other than the sample injection point, within a vaporization chamber such as outlined in the figures of the drawing. With reference first to FIG. 1, a vaporizing injector is schematically illustrated, which consists of, in a manner known per se, a heated outer support 10 and an inner liner, such as sintered glass.

For the application of the present invention, it is preferred that the liner 11 has an inner wall 12 provided with surface roughness for a better retention of the co-solvent. Furthermore, in the lower part, the liner 11 forms a sort of pocket 13 that is defined by the walls thereof, which are folded upwards to form a cone 14 for the open end of the column 15 to be introduced therein. In addition, the open end of the column 15 is preferably covered by a cap 16 held by projections 17, which avoids the risk that the liquid may be introduced in the column.

The injection is carried out by means of a syringe 18, with a needle 19, which is preferably operated by an automatic sampler. The syringe 18 first collects the sample 20, and then the co-solvent 21, with an air cushion 22 in case interposed there between.

The injection is started by introducing the needle 19 towards the bottom of the liner 11 (FIG. 1 on the left) and operating the piston 23 such that the co-solvent 21 is introduced in the bottom pocket 13 as much as possible. To the purpose, it is recommended that the needle 19 has a tip shaped such as illustrated in FIG. 2, for the co-solvent 21 to be introduced on the walls and in the bottom pocket 13 of the liner.

After the co-solvent has been injected, the sample is injected according to the usual procedure. Before injecting the sample, the syringe 18 can be lifted as shown in FIG. 1 on the right.

Alternatively, a syringe and a needle can be provided, which are particularly shaped in order to form two separate chambers, for the co-solvent and the sample, which are injected through a double needle, with separated ducts. In this case, the co-solvent and sample can be injected at the same time, though in different points in the vaporization chamber.

It should be noted that the co-solvent injection is suitably carried out at a higher speed than the sample injection, and possibly at least partially also while the needle is being moved from the lower to the upper points, if this movement is foreseen.

FIG. 3 illustrates a vaporization chamber 41 having an inner liner with various diameters, in order to define a first narrower space 42, where the co-solvent 43 deposits, and a second upper larger space 44, where the sample 45 is introduced and vaporized. Optionally a packing 16' is arranged at the bottom of the vaporization chamber.

Still in the case of vaporization injection, with PTV injector (Programmed Temperature Vaporisation), the carrier gas is advantageously fed through connections suitable to provide the backflush, in order to prevent the co-solvent and solvent from entering the column or pre-column during injection.

FIG. 4 illustrates a diagram of these connections, in the condition of active backflow, where the carrier gas 30 is deviated by the valve 31 in the duct 32 in order to be fed to column 34 and back to pre-column 35, which are connected to each other at the T-shaped connector 36. A part of the carrier gas reaches the injector 39, through the flow regulator 37 and the duct 38, and it is then eliminated through the splitting line 40.

As stated above, the co-solvent and sample are thus allowed to enter the column only when the injection has been completed, i.e. when the valve 31 is switched.

The invention claimed is:

1. A method for injecting a sample with co-solvent in a vaporization chamber or pre-column of a gas chromatograph, wherein the co-solvent is injected in advance of the sample into the vaporization chamber or pre-column separately from the sample, in a point other than the sample injection point by using a syringe wherein an air cushion is arranged between the sample and the co-solvent.

2. The method according to claim 1, wherein the co-solvent sample is injected in a point located more downstream than the sample injection point.

3. The method according to claim 1, wherein the sample is injected subsequently to the co-solvent, but before the co-solvent injected in advance is substantially evaporated.

4. The method according to claim 1, wherein the co-solvent is the same solvent composing the sample.

5. The method according to claim 1, wherein the co-solvent is different from the solvent composing the sample.

6. The method according to claim 5, wherein the co-solvent has a higher boiling than the solvent composing the sample.

7. The method according to claim 1, wherein the sample injected is in the form of a gas or vapour and the co-solvent is a liquid.

8. The method according to claim 1, for injection in a split/splitless injector (SSL) vaporizing injector, wherein the temperature in the vaporization chamber is kept substantially uniform and higher than the boiling point of the solvent and co-solvent, wherein the co-solvent is injected in advance of the sample.

9. The method according to claim 1, wherein the injection is carried out in a PTV injector, wherein the co-solvent is injected more downstream than the sample.

10. The method according to claim 9 for injection in an elongated programmed temperature vaporisation (PTV) vaporization chamber having a connection with a free end of a gas chromatography column or pre-column at a first end thereof, wherein the co-solvent is injected in proximity of a first end of the vaporization chamber and the sample is injected in a point closer to another end of the vaporization chamber.

11. The method according to claim 9, wherein the co-solvent is injected with a bent spray needle.

12. The method according to claim 1, wherein during the injection, the temperature in the vaporization chamber or pre-column is selected to have a high vaporization of the solvent and a small evaporation of the co-solvent.

13. The method according to claim 12, wherein the temperature in the vaporization chamber or pre-column, when the solvent composing the sample has been completely eliminated, is increased for the substances to be analysed and the co-solvent to be transferred in the gas chromatography column.

14. The method according to claim 1, wherein the co-solvent injection speed and the sample injection speed are different.

15. The method according to claim 1, wherein one or more additional injections of co-solvent are carried out by being intercalated with one or more sample injections.

16. An apparatus for gas chromatographic analysis, comprising a gas chromatography column housed in an oven, an injector for introducing samples in a vaporization chamber, or a pre-column, a detector and a sampler that serves the injector, wherein the sampler provides means for carrying out two separate injections, at different points according to the method of claim 1 by using a syringe wherein an air cushion is arranged between the sample and the co-solvent.

17. The apparatus according to claim 16, wherein the sampler provides means for carrying out injections at different and pre-selectable speeds and with programmable speed gradients.

18. The apparatus according to claim 16, wherein a packing is arranged at the bottom of the vaporization chamber.

19. The apparatus according to claim 16, comprising a PTV vaporising injector provided with an inner liner and independent heating means, as well as means for introducing sample vapours in a gas chromatography column or pre-column having an open end in said inner liner, wherein the inner wall of said liner is at least partially provided with surface roughness.

20. The apparatus according to claim 19, wherein the inner liner defines a passage having an end portion, in the direction of the column or pre-column, which is narrower than an above passageway.

21. The apparatus according to claim 19, wherein a free end of the column or pre-column inside said liner is surmounted by a dome-shaped cap.

22. The apparatus according to claim 19, wherein the injector is fed with carrier gas through connections suitable to provide a backflush, to prevent the co-solvent or solvent to enter the column or pre-column throughout the injection time.

* * * * *